United States Patent [19]

Capozza

[11] 4,186,185
[45] Jan. 29, 1980

[54] COMPOSITIONS COMPRISING ARYLENE SUBSTITUTED POLY(ORTHOESTERS) CONTAINING USEFUL AGENTS

[75] Inventor: Richard C. Capozza, Palo Alto, Calif.

[73] Assignee: Alza Corporation, Palo Alto, Calif.

[21] Appl. No.: 972,737

[22] Filed: Dec. 26, 1978

Related U.S. Application Data

[60] Division of Ser. No. 837,308, Sep. 28, 1977, Pat. No. 4,136,252, which is a continuation-in-part of Ser. No. 675,185, Apr. 8, 1976, Pat. No. 4,066,747.

[51] Int. Cl.$^2$ .................. A61K 9/22; A61K 31/74
[52] U.S. Cl. .................................. 424/19; 424/78
[58] Field of Search ..................... 424/19, 32, 78

[56] References Cited

U.S. PATENT DOCUMENTS

| | | | |
|---|---|---|---|
| 4,052,505 | 10/1977 | Higuchi et al. | 424/19 |
| 4,115,544 | 9/1978 | Shell | 424/19 |

*Primary Examiner*—Frederick E. Waddell

*Attorney, Agent, or Firm*—Paul L. Sabatine; Thomas E. Ciotti; Edward L. Madell

[57] ABSTRACT

This invention concerns polymeric orthoesters having a repeating mer comprising a hydrocarbon radical and an orthoester functionality of the general formula:

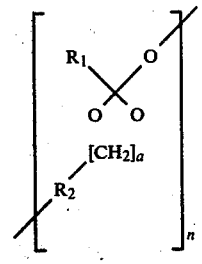

wherein $R_1$ is a monovalent radical, $R_2$ is a hydrocarbon radical, a is 2 to 3, and n is at least 10. The polymers are useful for making articles of manufacture and as coatings for beneficial agents.

8 Claims, 1 Drawing Figure

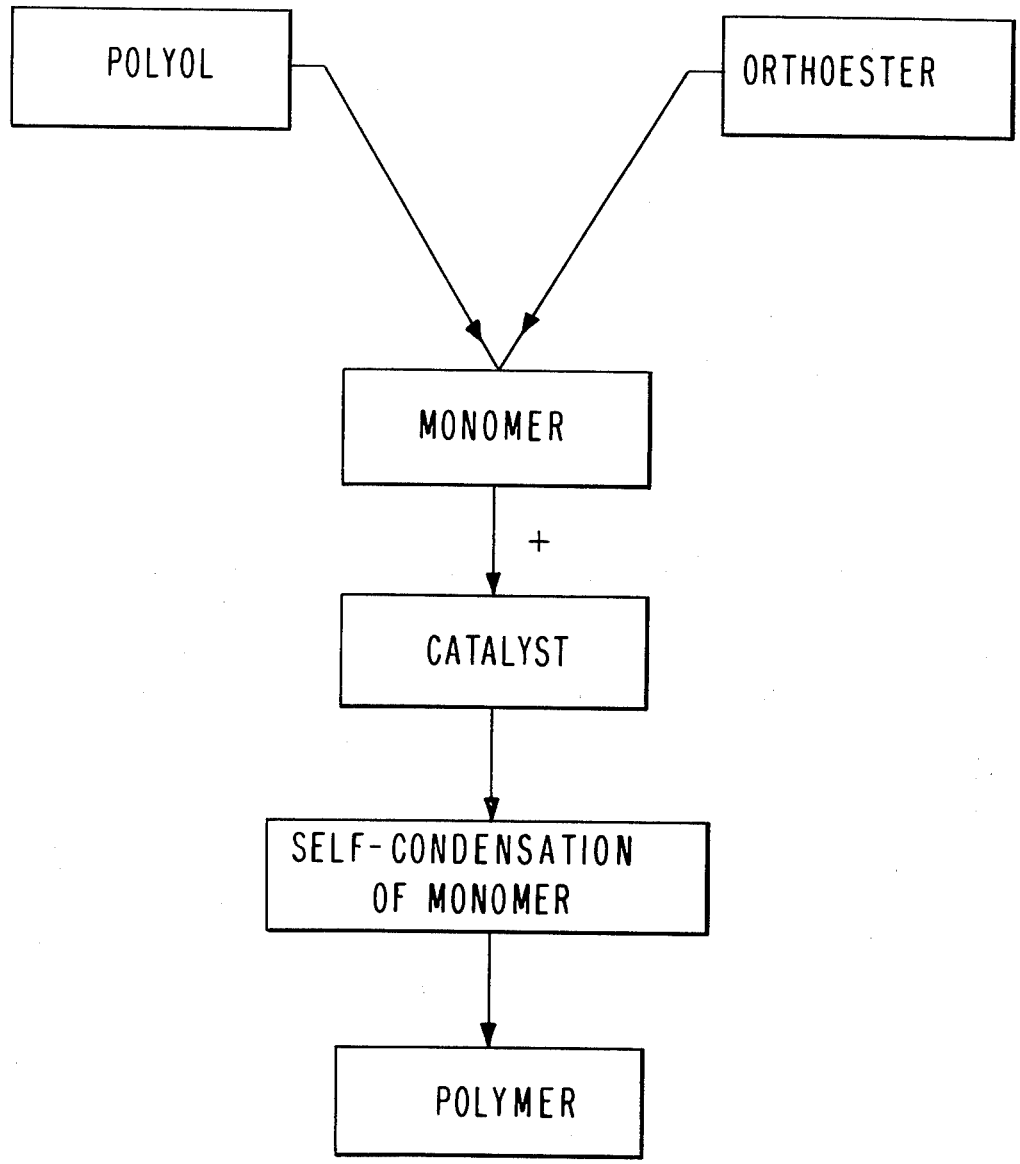

COMPOSITIONS COMPRISING ARYLENE SUBSTITUTED POLY(ORTHOESTERS) CONTAINING USEFUL AGENTS

CROSS-REFERENCE TO RELATED APPLICATIONS

This application is a division of U.S. patent application Ser. No. 837,308, filed on Sept. 28, 1977, and now U.S. Pat. No. 4,136,252 issued on Jan. 23, 1979 which application Ser. No. 837,308 is a continuation-in-part of U.S. patent application No. 675,185, filed on Apr. 8, 1976 and now U.S. Pat. No. 4,066,747, issued on Jan. 3, 1978. These applications are incorporated herein by reference and benefits of their filing dates are claimed. This application and applications Ser. Nos. 837,308 and 675,185 are assigned to the ALZA Corporation of Palo Alto, Calif.

BACKGROUND OF THE INVENTION

1. Field of the Invention

The present invention relates to polymers. More particularly, the invention pertains to novel and useful polymers comprising a mer formed of a dioxycarbon moiety having one of its oxygens an integral member of a heterocyclic ring and the other oxygen bonded to a repeating mer. The polymers are represented by the following general formula:

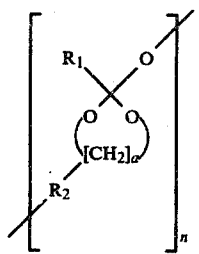

wherein $R_1$ is hydrogen, alkyl, alkenyl, cycloalkyl, cycloalkyl substituted with an alkyl, alkenyl or alkoxy, cycloalkenyl, cycloalkenyl substituted with an alkyl, alkenyl or alkoxy, aryl, alkaryl and aryl substituted with alkyl, alkenyl and alkoxy; $R_2$ is an alkylene, alkenylene, cycloalkylene, cycloalkylene substituted with an alkyl, alkylene, alkenyl or alkoxy, cycloalkenylene, cycloalkenylene substituted with alkyl, alkylene, alkenyl or alkoxy, arylene, or arylene substituted with alkyl, alkylene, alkenyl or alkoxy. The generic formula also embraces in addition to homopolymers, copolymers of the random and block types formed by reacting monomers or mixtures of preformed homopolymers and/or copolymers, branched polymers and cross-linked polymers. In the above formula a is 2 to 3, and n is greater than 10, usually 10 to 100,000.

2. Description of the Prior Art

The reaction of orthoesters with glycols leading to non-polymeric and other diverse products is known to the art in the references such as *Ind. J. Appl. Chem.*, Vol. 28, No. 2, pages 53 to 58, 1965 wherein Mehrota, et al obtained monoethoxy-monoglycolate and triglycoxy-bisorthoformate by reacting orthoformate with hexamethylene glycol in molar ratios of one to one, and two to three to yield low molecular weight compounds. Similarly, Crank, et al in *Aust. J. Chem.*, Vol. 17, pages 1392 to 1394, 1964, disclosed the reaction of triols with orthoesters including ethyl orthoformate with butane-1,2,4-triol, pentane-1,2,5-triol and pentane-1,3,5-triol to form monomeric bicyclic compounds. During the preparation of the bicyclic orthoesters by reacting ethyl orthoformate with triols, Crank, et al found that compounds produced from starting materials having a 1,2-diol structure also contained compounds having ethylene linkages. In a subsequent paper, Crank et al *Aust. J. Chem.*, Vol. 17, pages 1934 to 1938, 1964, developed this reaction into a synthetic procedure for the conversion of 1,2-diols into olefins. Later, DeWolfe in Carboxylic Ortho Acid Derivatives, 1970, published by Academic Press, Inc., New York, noted that carboxylic orthoesters are more reactive toward acid hydrolysis than almost any other class of compounds, and this high hydrolytic reactivity complicates their synthesis and storage. DeWolfe reported that the conversion of diols to cyclic orthoesters including alkoxydioxolane or alkoxydioxane, followed by acid hydrolysis, provides a method for monoacylating diols. More recently, Bailey reported in *Poly. Prepr. Amer. Chem. Soc. Div. Polym. Chem.*, Vol. 13, No. 1. pages 281 to 286, 1972, that the polymerization of spiro orthoesters at ambient and elevated temperatures led to polyesters and polycarbonates of the structures [—$CH_2CH_2CH_2COOCH_2CH_2O$—]$_n$ and [—$OCH_2OCOOCH_2CH_2CH_2$—]$_n$. In copending U.S. patent application Ser. No. 544,808 filed Jan. 28, 1975 and assigned to the same assignee of this application, inventors N. Choi and J. Heller disclosed orthoester and orthocarbonate polymers comprising a polymeric backbone having a dioxycarbon unit with a multiplicity of hydrocarbon groups bonded thereto. The polymers of Choi and Heller have both oxygens of the dioxycarbon backbone formed independently of a heterocyclic ring.

SUMMARY OF THE INVENTION

The invention concerns a novel class of polymeric orthoesters, comprising a repeating unit consisting of an orthoester function and a hydrocarbon radical. The orthoester embraces a dioxycarbon having one of its oxygen atoms formed integral in a heterocyclic oxa ring, to form preferably dioxolane or dioxane rings, and its other oxygen bonded to a repeating mer. The polymers have a controlled degree of hydrophobicity with a corresponding controlled degree of erosion in aqueous and aqueous-like environments to innocuous products. The polymers can be synthesized by conventional techniques into assorted articles of manufacture having various shapes and sizes adapted for the environment of use, and they can be used as coating for the controlled release of beneficial agents.

SUMMARY OF FLOW FIGURE

The flow FIGURE accompanying the application indicates the polymers of the invention are synthesized by reacting a polyol with an orthoester to form a monomer, which is then polymerized in the presence of a catalyst to yield the polyorthoester.

DETAILED DESCRIPTION OF THE INVENTION

The phrases "monovalent radical" and "multivalent hydrocarbon radical" appearing above and as used elsewhere in the specification, includes for the purpose of this invention, the terms embraced by $R_1$ and $R_2$ as defined below.

The term "alkyl" embraces straight and branched chain alkyl radicals of 1 to 20 carbon atoms such as methyl, ethyl, n-propyl, n-butyl, n-amyl, n-hexyl, n-heptyl and the various positional isomers thereof such as isopropyl, t-butyl, sec-butyl, isoamyl, isohexyl, t-heptyl, and the like. The term "alkylene" denotes straight or branched chain divalent alkylene radicals of 1 to 20 carbon atoms inclusive such as 1,2-ethylene, 1,3-propylene, 1,4-butylene, 1,5-penylene, 1,6-hexylene, and the like.

Exemplary alkenyls include straight and branched chain lower alkenyl groups of 2 to 20 carbon atoms such as 1-propenyl, 2-propenyl, 1-butenyl, 2-butenyl, 1-pentenyl, 2-ethenyl, and the corresponding positional isomers such as 1-isobutenyl, 2-isobutenyl, 2-sec-butenyl, 2-methyl-1-butenyl, 2-methyl-2-pentenyl, 2,3-dimethyl-3-hexenyl, and the like. The term "alkenylene" denotes an unsaturated straight or branched chain divalent radical of 2 to 20 carbon atoms such as 1,3-propyl-1-ene, 1,4-but-2-enylene, 1,5-pent-2-enylene and 1,6-hex-3-enylene.

The term "alkoxy" includes the straight and branched chain lower alkoxy groups and the positional iosmers thereof having 1 to 20 carbon atoms, for example, methoxy, ethoxy, propoxy, butoxy, n-pentoxy, n-hexoxy, isopropoxy, 2-butoxy, isobutoxy, 3-pentoxy, and the like.

The term "cycloalkyl" as used in this specification includes monocyclic, lower cycloalkyl radicals of 3 to 8 carbon atoms such as cyclopropyl, cyclobutyl, cyclopentyl, cyclohexyl, and cycloheptyl. The term "cycloalkylene" includes monocyclic, lower cycloalkylene radicals of 3 to 8 carbons such as cyclopropylene, cyclobutylene, cyclopentylene, cyclohexylene and cycloheptylene. Similarly, the phrase "cycloalkyl" or "cycloalkylene substituted with an alkyl of 1 to 20 carbons, an alkenyl of 2 to 20 carbons, an alkoxy of 1 to 20 carbons, and an alkylene of 1 to 20 carbons" include substituted cycloalkyl and cycloalkylene such as 2-methyl-1,3-cyclopropylene, 2-methyl-1,4-cyclopentylene, 2-methyl-1,6-cyclohexylene, 2-ethoxy-2,3-cyclopropylene, 5-butoxy-1,4-cyclopentylene, 2-isobutenyl-1,4-cyclohexylene, 2-methyl cyclohexyl, 3-ethyl cyclohexyl, 1,4-cyclohexyldimethylene, 1,4-cyclohexyldihexylene, and the like.

The term "cycloalkenyl" includes monocyclic cycloalkenyl having from 4 to 8 carbons as ring members such as cyclopent-2-enyl, cyclopent-3-enyl, cyclohex-2-enyl and cyclohex-2-enyl. The term "cycloalkenylene" includes monocyclic cycloalkenylenes of from 4 to 8 carbons such as 1,4-cyclopent-2-enylene, 1,5-cyclopent-3-enylene, 1,6-cyclohex-2-enylene, and 1,6-cyclohex-2-enylene. The phrase "substituted cycloalkenyl or cycloalkenylene" includes cycloalkenyl and cycloalkenylene substituted with an alkyl of 1 to 20 carbons, an alkenyl of 2 to 20 carbons, an alkoxy of 1 to 20 carbons, and an alkylene of 1 to 20 carbons such as 4-methyl-cyclohex-2-enyl, 5-methyl-cyclohex-2-enyl, 5-methyl-(1,4-cyclopent-2-enylene), 6-ethyl-(1,4-cyclohex-2-enylene), 6-ethoxy-(1,5-cyclohex-2-enylene), 2-ethyl-(1,4-cyclohex-2-enylene), 6-ethoxy-(1,5-cyclohex-2-enylene), 2-methoxy-(1,4-cyclohex-2-enylene), 1,4-cyclohex-2-enyldi-methylene, and the like.

The terms "aryl" and "arylene" as used herein denote a member having from 6 to 36 carbon atoms. The terms include a member selected from the group consisting of phenyl, phenylalkylene, phenylalkenylene, phenyldialkenylene, phenylene, naphthyl, naphthylene, and these groups substituted with an alkyl of 1 to 20 carbons, an alkenyl of 2 to 20 carbons, an alkoxy of 1 to 20 carbons and alkylene of 1 to 20 carbons. Typical groups include phenyl, 1,4-phenylene, 1,4-phenyldimethylene, 1,4-phenyldiethylene, 2-methylphenyl, 2-ethyl-1,4-phenyldimethylene, 1-phenylethylene, 2-butylphenyl, 4-ethoxyphenyl, 1-methylenephenyl or benzyl, 2-methyl-1,4-phenyldimethylene, 2-methoxy-1,4-phenyldimethylene, 2-propyl-1,4-phenyldiethylene, naphthyl, 2-methylnaphthylene, 2,5-dimethyl-naphthylene, and the like.

The novel polymers of the invention are synthesized by intimately contacting and reacting at least one starting polyol with at least one starting orthoester to yield a monomer that is then polymerized in the presence of a catalyst to yield the corresponding polymer.

Exemplary polyols suitable as starting reactants include triols and the like that can enter into the polymerization reaction without adversely affecting it, or the polymeric product. The polyols are known to the art in reported synthesis and they are commercially available. Generally, they include straight and branched chain triols and the like. Representative polyols include 1,2,3-propanetriol, 1,3,4-butanetriol, 1,4,5-pentanetriol, 1,5,6-hexanetriol, 1,2,5-pentanetriol, 1,3,5-pentanetriol, 1,2,4-butanetriol, 2-methyl-1,2,3-propanetriol, 2-ethyl-1,2,3-propanetriol, 2-methoxy-1,3,4-butanetriol, 3-phenyl-1,4,5-pentanetriol, 2-isopropyl-3-methyl-1,4,5-pentanetriol, β-methylglycerol, 2-hydroxymethyl-1,4-butanediol, 2-hydroxymethyl-1,5-pentanediol, 2-hydroxymethyl-1,6-hexanediol, 1-(1',2'-dihydroxyethyl)-4-hydroxymethylbenzene, 2-hydroxymethyl-1,4-butanediol, 2-hydroxymethyl-1,5-pentanediol, 1,2,8-trihydroxyoct-5-ene, 1-hydroxymethyl-4-(2',3'-dihydroxy-n-propyl)-benzene, and the like. The preparation of the above polyols is known to the art in *Acta Pharm. Jugoslav.*, Vol. 2, pages 134 to 139, 1953; *Ann.*, Vol. 594, pages 76 to 88, 1955; *J. Am. Chem. Sco.*, Vol. 71, pages 3618 to 3621, 1949; *ibid.*, Vol. 74, pages 2674 to 2675, 1952; *Chem. Abst.*, Vol. 42, pages 8774 to 8775, 1948; *ibid.*, Vol. 43, pages 571 to 573, and 6652, 1949; *ibid.*, Vol. 44, pages 2554 to 7231, 1953; *ibid.*, Vol. 46, page 9585, 1952; *ibid.*, Vol. 47, page 7575, 1953; *ibid.*, Vol. 48, page 106, 1954; *ibid.*, Vol. 49, pages 6098 to 6099, 1955; *Encyclopedia of Chemical Technology*, Kirkothmer, Vol. 10, pages 638 to 678, 1966, published by Interscience Publishers, New York.

Exemplary starting orthoesters include simple and mixed orthoesters of the formula $R_3C(OR_4)$ wherein $R_3$ is hydrogen, alkyl, alkenyl, cycloalkyl, cycloalkenyl, and aryl as defined above, and $R_4$ is alkyl, alkenyl, cycloalkyl, cycloalkenyl, and aryl as defined above. Representative esters include trimethyl orthoformate, tri-n-butyl orthoformate, tri-n-hexyl orthoformate, dibutylmonoethyl orthoformate, sec-butyldiethyl orthoformate, methyldiethyl orthoformate, ethyldi-isopropyl orthoformate, di-isopropylbutyl orthoformate, ethylorthoacetate, methylorthoacetate, ethylorthopropionate, methylorthopropionate, sec-butylorthopropionate, propylorthopropionate, tricyclohexyl orthoformate, triphenyl orthoformate, dimethylethenyl orthoformate, diethylpropenyl orthoformate, di-isopropyl-ethenyl orthoformate, dimethylisobutenyl orthoformate, 1,1,1-trimethoxy-prop-2-ene, α,α,α-trimethoxytoluene, 1-methyl-2-(trimethoxymethyl)benzene, trimethyl orthoacetate, trimethyl orthopropionate, trimethyl orthobutyrate, and the like.

The above orthoesters and like orthoesters can be prepared according to the following preparations. The Pinner synthesis as described in Ber., Vol. 16, pages 352 to 363, 1883; and ibid., pages 1644 to 1663, 1883, wherein an appropriate nitrile is reacted with an equivalent amount of dry hydrogen halide and an equivalent amount of alcohol to form an iminoester hydrohalide. This is then alcoholized with an excess of alcohol to form the orthoester. The Pinner reaction is set forth as follows:

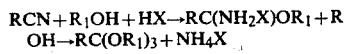
$RCN + R_1OH + HX \rightarrow RC(NH_2X)OR_1 + ROH \rightarrow RC(OR_1)_3 + NH_4X$ Orthoesters suitable for the purpose of the invention also can be preapared by the Mkhitaryan reaction as described in Gen. Chem., U.S.S.R., Vol. 8, pages 1361 to 1367, 1938, wherein an alkoxy group of a readily available orthoester such as triethyl orthoacetate or formate are replaced by a higher boiling alcohol or polyol according to the general reaction:

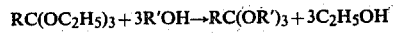
$RC(OC_2H_5)_3 + 3R'OH \rightarrow RC(OR')_3 + 3C_2H_5OH$

The orthoesters may also be prepared by alcoholysis of trihaloalkyl groups as set forth in J. Am. Chem. Soc., Vol. 54, pages 2964 to 2966, 1932; as indicated by the following reaction:

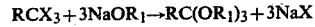
$RCX_3 + 3NaOR_1 \rightarrow RC(OR_1)_3 + 3NaX$

The preparation of orthoesters also is known to the art with ample description of various methods of preparation in U.S. Pat. Nos. 2,409,699; 2,867,667; 3,323,925; and 3,546,188; and in British Pat. Nos. 853,405; and 1,099,559. Also, in Synthetic Organic Chemistry, Chapter 16, pages 542 to 545, 1953, published by John Wiley and Sons; in The Chemistry of the Aliphatic Orthoesters, Chapter 2, pages 11 to 43, 1943, Reinhold Publishing Corp.; in Encyclopedia of Chemical Technology, Kirk-Othmer, Vol. 8, pages 365 to 383, 1965, Interscience Publishers, New York; Recueil Trav. Chem. Pays. Bes. Vol. 88, pages 897 to 904, 1909; J. Am. Chem. Soc., Vol. 64, pages 1825 to 1927, 1942; Ind. Eng. Chem. Prod. Res. Develop., Vol. 10, No. 4, pages 425 to 428, 1971; J. Am. Chem. Soc., Vol. 71, pages 40 to 46, 1949; Ann. Chem., Vol. 675, page 142, 1964; Agnew. Chem., Vol. 69, page 371, 1957; J. Am. Chem. Soc., Vol. 76, pages 5736 to 5739, 1954; ibid., Vol. 77, pages 5601 to 5606, 1955; Chem. Ber., Vol. 89, page 2060, 1956; Aust. J. Chem., Vol. 17, pages 1385 to 1398, 1964; Gazz. Chem. Ital., Vol. 96, page 1164, 1966; Chem. Commum., page 13, 1967; and Carboxylic Ortho Acid Derivatives, Chapter 1, pages 1 to 133, 1970, published by Academic Press, New York. The orthoesters can also be prepared by conventional techniques including alcoholysis, condensation, elimination and reduction reactions as described in Organic Functional Group Preparations, by Sandler and Karo, Vol. II, Chapter 2, pages 41 to 68, 1971, published by Academic Press.

The novel polymers of the invention are synthesized by first intimately contacting and reacting a starting polyol with a starting orthoester to form a monomer. Then, the monomer is polymerized to yield the corresponding polymer. Generally, the first reaction is carried out by reacting stoichiometric amounts, or an excess of polyol with stoichiometric amounts or excess of orthoester to yield the monomer. The amount of each can be from about 1 to 10 moles of polyol to about 1 to 10 moles of orthoester. The polyol and the orthoester are reacted under an inert atmosphere, usually nitrogen or argon, at 60° C. to 150° C. for 1 to 96 hours. The reaction also produces an alcohol that is distilled off into a collection flask. The monomer is purified by vacuum fractionation over a drying agent, for example, CaO. Next, the monomer is added to a flask that was purged with an inert gas, a polymerization catalyst is added to the flask and the temperature raised to 90° to 180° for ½ to 24 hours and the condensate formed collected in a side flask. Then, the pressure is reduced and the polymerization continued at 60° C. to 180° C. and 0.01 to 0.0001 mm mercury while maintaining the elevated temperature and reduced pressure carrying out the polymerization by continuously mixing the monomer for 2 to 96 hours to yield the polymer. A flow diagram indicating the reaction steps necessary to synthesize the polymer is set forth in the accompanying FIGURE. In the FIGURE, the necessary steps are briefly indicated as the reaction of the polyol with the orthoester to yield the monomer followed by self-polymerization of the monomer to yield the polymer.

The polymer is recovered under anhydrous conditions from the reaction vessel by conventional isolation and recovery techniques. For example, the polymer is recovered while hot by extruding or pouring, or the polymer is isolated after cooling, by dissolving it in a dry organic solvent such as benzene, carbon tetrachloride, methylene chloride, dioxane, toluene or xylene, followed by the addition of an organic liquid in which the polymer is insoluble or has limited solubility to precipitate the polymer. Organic liquids for this purpose include ether, hexane, pentane, petroleum ether, hexane, heptane mixtures, and the like. The polymer is isolated by filtering and drying under anhydrous conditions. Other methods for recovering the polymer include lyophilizing from a solvent.

Representative catalysts for performing the polymerization reaction are Lewis acids such as boron trifluoride, boron trichloride, boron trichloride eterate, boron trifluoride etherate, stannic oxychloride, phosphorous oxychloride, zinc chloride, phosphorous pentachloride, calcium acetate, antimonous oxide mixture, antimony pentachloride, antimony pentafluoride, stannous octoate, stannic chloride, diethyl zinc, n-butyl lithium, and mixtures thereof. The catalysts also include Bronsted catalysts such as p-toluene sulfonic acid, polyphosphoric acid, cross-linked polystyrene sulfonic acid, acidic silica gel, and mixtures thereof. Other catalysts include neutral or basic catalysts such as tetrabutyl titanate, and titanium sodium hydrogen hexabutoxide. The amount of catalyst used is about one part catalyst to about 500 parts of the ester monomer. Smaller or larger amounts can also be used, such as 0.005% to about 2.0% based on the weight of the starting monomer.

The polymerization optionally can be carried out in the presence of an inert organic solvent that does not adversely affect the reaction, or the reaction can proceed in the absence of added solvent. In the latter reaction one of the reactants, for example, the polyol initially serves as the solvent. As polymerization proceeds, solvent by-product is removed from the reaction by conventional distillation, azeotropic distillation, or by distillation under vacuum. Suitable azeotropic solvents include toluene, benzene, m-xylene, cumene, pyridine, and n-heptane.

The following examples are set forth as representative methods illustrative of the spirit of the present invention. These examples are not to be construed so as to limit the scope of the invention, as these and other functionally equivalent means will be readily apparent to those skilled in the subject art.

EXAMPLE 1

To 59.72 grams (0.655 moles) of anhydrous 1,2,3-propanetriol in a 500 milliliter 3-necked borosilicate flask equipped with a stirrer, a nitrogen inlet and a Vigreaux column, was added with constant stirring under a nitrogen atmosphere 97.9 (0.660 moles) of anhydrous triethylorthoformate and the reactants permitted to react for 6 hours. The reaction was carried out at atmospheric pressure, and at 130° C.±2° C. During the reaction, approximately a stoichiometric amount of ethanol was distilled from the reaction vessel. Next, the product was transferred to a 250 milliliter Bantam flask for vacuum fractionation over CaO, with the main fraction collected at 67°–85° C. under 0.5 millimeters of mercury. The fraction as analyzed by gas chromatography has a purity of 90% and it contained both the cis and trans isomers. An infrared analysis did not show any carbonyl peaks. Finally, the product was redistilled from triethylamine to yield pure monomer, 2-ethoxy-4-hydroxy-methyl-1,3-dioxolane.

Next, to 6.3 grams (0.043 moles) of the monomer in a polymerization reactor was added 5 milligrams of p-toluene sulfonic acid and the vessel heated to 130° C. for 1 hour with collection of any formed condensate. Then, while maintaining this temperature, the pressure was gradually reduced to 0.05 millimeters of mercury, and at this reduced pressure, the temperature was slowly raised to 135° C. The self-condensation polymerization of the monomer was continued under this condition for 4 hours to yield the polymer. The polymer was isolated from the reactor, and it had the following structure wherein n is the degree of polymerization and is greater than 10.

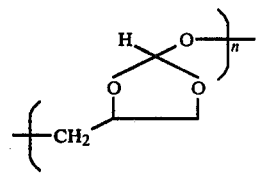

EXAMPLES 2 TO 10

The procedure of Example 1 is repeated in the present example with all conditions substantially as described except that in Table 1, a different polyol is reacted with an orthoester to form a monomer that is then polymerized to a novel polymer. In Table 1, "OL" refers to polyol, "OE" to orthoester, "M" denotes monomer, and "P" refers to polymer. Also, in the table, "Me" is methyl, "Et" is ethyl, "pr" is propyl, and "Bu" is n-butyl.

TABLE I

| Ex. | OL | OE | M | P |
|---|---|---|---|---|
| 2 | CH₂OH−H₂C−C(OH)−CH₂−CH₂−OH | HC(OEt)₃ | dioxolane with (CH₂)₂OH, H, OEt | polymer with −(CH₂)₂− |
| 3 | CH₂OH−H₂C−C(OH)−CH₂−CH₂−CH₂−OH | HC(OEt)₃ | dioxolane with (CH₂)₃OH, H, OEt | polymer with −(CH₂)₃− |
| 4 | CH₂OH−H₂C−CH−CH₂−CH₂−CH₂−CH₂ with OH | HC(OEt)₃ | dioxolane with (CH₂)₄OH, H, OEt | polymer with −(CH₂)₄− |
| 5 | H₂C−CH−CH₂−CH₂ with OH OH OH | HC(OEt)₃ | dioxolane with (CH₂)₂OH, H, OEt | polymer with −(CH₂)₂− |

TABLE I-continued

| Ex. | OL | OE | M | P |
|---|---|---|---|---|
| 6 | H₂C—CH—CH₂—CH₂—CH₂ with OH OH (on first two C) and OH (on last C) | HC(OEt)₃ | (CH₂)₃OH group on dioxolane ring with H, OEt | Polymer: dioxolane with (CH₂)₃ bridge, H, capping |
| 7 | H₂C—CH—(CH₂)₂CH=CH(CH₂)₂OH with OH on CH₂ and CH | HC(OPr)₃ | H, OPr dioxolane with HO(CH₂)₂—CH=CH—(CH₂)₂ chain | Polymer with —(CH₂)₂—CH=CH—(CH₂)₂— repeat |
| 8 | H₂C—CH—CH₂ with OH OH OH | CH₂=CH, OCH₃, CH₃O, OCH₃ on central C | CH₂=CH, OCH₃ dioxolane, HOCH₂ | Polymer: CH₂=CH dioxolane, H₂C repeat |
| 9 | H₂C—CH—CH₂ with OH OH OH | Phenyl—C(OCH₃)(CH₃O)(OCH₃) | Phenyl dioxolane OCH₃, HOCH₂ | Phenyl dioxolane polymer, CH₂ repeat |
| 10 | H₂C—CH—CH₂ with OH OH OH | CH₃-tolyl—C(OCH₃)(CH₃O)(OCH₃) | CH₃-tolyl dioxolane OCH₃, HOCH₂ | CH₃-tolyl dioxolane polymer, CH₂ repeat |

EXAMPLES 11 TO 16

The procedure of Example 1 is repeated in the present example leading to an orthoester polymer of the following general formula:

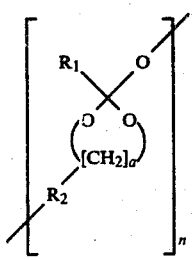

wherein $R_1$ is a member selected from the group consisting of hydrogen, alkyl, alkenyl, cycloalkyl, cycloalkenyl, aryl, and aralkylene, and $R_2$ is an arylene. A polymer embraced by the formula above having an arylene arrangement for polymeric growth at $R_2$ is prepared by using starting polyols of the following formula:

(a) HO—(R₂)ₙ—R₃—CH(OH)—CH₂OH and (b) HO—(R₂)ₙ—R₃—CH(CH₂OH)—CH₂OH wherein $R_2$ is alkylene or alkenylene, $R_3$ is phenyl or nahpthyl, and $n$ is 0 to 20. Polymeric orthoesters prepared according to these examples are set forth in Table 2.

TABLE II

| Example | OL | OE | M | P |
|---|---|---|---|---|
| 11 | 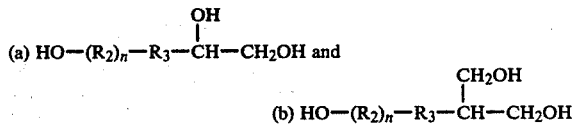 | | | |

TABLE II-continued

| Example | OL | OE | M | P |
|---|---|---|---|---|
| 12 | HOCH₂-C₆H₄-CH₂-CH(OH)-CH₂OH | HC(OMe)₃ | (orthoester of structure with OMe, dioxolane ring attached to para-CH₂-C₆H₄-CH₂OH) | polymer [-CH₂-C₆H₄-CH₂-(dioxolane)-]ₙ |
| 13 | HO-CH₂-C₆H₃(CH₃)-CH(OH)-CH₂OH | HC(OEt)₃ | (OEt dioxolane on methyl-substituted benzyl alcohol) | polymer, methyl-substituted |
| 14 | HO-CH₂-C₆H₃(CH₃)-C(CH₂OH)(CH₂-CH₂OH) | HC(OEt)₃ | (OEt 1,3-dioxane on methyl-substituted benzyl alcohol) | polymer |
| 15 | HO-CH₂-naphthyl-CH(OH)-CH₂OH | HC(OMe)₃ | (OMe dioxolane on naphthyl-CH₂OH) | polymer |
| 16 | HO-(CH₂)₂-naphthyl-CH(CH₂OH)-CH₂OH | HC(OEt)₃ | (OEt 1,3-dioxane on naphthyl-(CH₂)₂OH) | polymer |

APPLICATION OF THE INVENTION

The orthoester polymers prepared according to the mode and manner of the invention are useful for coating beneficial agents that can be released at a controlled and continuous rate over a prolonged period of time. The phrase "beneficial agent" as used in the specification and accompanying claims includes pesticides, herbicides, germicides, biocides, algicides, rodenticides, fungicides, insecticides, plant growth promoters, plant growth inhibitors, preservatives, disinfectants, cosmetics, drugs, plant foods, vitamins, sterilants, plant hormones, fertility inhibitors, fertility promoters, air purifiers, micro-organism attenuators, and nutrients.

The term "drug" as comprehended by beneficial agent, braodly includes physiologically or pharmacologically active substances for producing a localized or systemic effect or effects in mammals, including warm blooded animals, humans and primates, avians, valuable domestic household, zoo, sport or farm animals such as sheep, goats, cattle, horses, etc., or for administering to laboratory animals such as mice, rats and guinea pigs. That is, the polymers of the invention can be used for administering drugs that are active at a point in near relation to the delivery site, or, for administering drugs which will produce a response at a site remote from the point of application. The drugs that may be administered include inorganic and organic drugs without limitation, are those drugs that can be transported across a vessel, for example, drugs acting on the central nervous system such as hypnotics and sedatives, narcotic antagonists, psychic energizers, tranquilizers, anticonvulsants, muscle relaxants, anti-parkinson agents, antipyretics, anti-inflammatory, local anesthetics, antispasmodics, antiulcer, antimicrobials, antimalarials, antivirals, hormonal, sympathomimetic, cardiovascular, diuretics, antiparasitic, neoplastic, hypoglycemic, essential amino acids, essential elements, and ophthalmic drugs. The above drugs are described in *The Pharmacological Basis of Therapeutics*, edited by Goodman and Gilman, 4th Edition, 1970, published by the Macmillan Company; and in *The Drug, The Nurses, The Patient,* by Falconer, Ezell, Patterson and Gustafson, 5th Edition, 1974, published by W. B. Saunders Company.

The agents can be in various forms, such as uncharged molecules, components of molecular complexes, salts such as hydrochloride, hydrobromide, sulfate, laurates, palmitates, phosphate, nitrate, borate, acetate, maleate, tartrate, oleates, and salicylates. For acidic agents, salts of metals, amines, or organic cations, for example quaternary ammonium, can be employed. Furthermore, simple derivatives such as esters, ethers, and amides which have solubility characteristics compatible with the polymer are suitable for the purpose of the invention. Also, an agent that has limited solubility or is water insoluble can be used in a form that is a water soluble derivative thereof to effectively serve as a solute, and on its release from the polymer, it is converted by the environment including enzymes, hydrolyzed by body pH, or metabolic processes to the original form or to an active form. Additionally, agent within the polymers can have various art known forms such as solution, dispersion, paste, cream, particle, granule, emulsions, suspensions, and powders.

The orthoester polymers are useful in a presently preferred embodiment for manufacturing polymeric compositions containing drug which composition bioerodes in a biological aqueous environment with an accompanying release of drug. For example, a composition is prepared by heating the polymer of Example 1 until it becomes pliable, about 90° C. to 140° C., and then adding micronized hydrocortisone to the polymer. Next, the polymer and the hydrocortisone are thoroughly mixed to produce a good dispersion of the drug, and to yield a 5% hydrocortisone loaded polymer. After the polymer drug formulation cools to room temperature, the formulation can be molded into preselected designs that are sized, shaped and adapted for positioning and placement in the environment of use. A formulation containing hydrocortisone can be used for the management of inflammation and bursitis when applied to a drug receptor site.

Other drugs that can be mixed with the orthoester polymers include ophthalmic drugs selected from the group consisting of pilocarpine, pilocarpine and its therapeutically acceptable salts such as pilocarpine hydrochloride and pilocarpine nitrate, eserine salicylate, atropine sulfate, homatropine and eucatropine; hormonal agents selected from the group consisting of prednisolone, cortisone, cortisol, triamcinolone, 17β-estradiol, ethynyl estradiol, 17α-hydroxyprogesterone acetate, 19-nor-progesterone, norethindone progesterone and other progestational and estrogenic steroids; sympathomimetic drugs selected from the group consisting of epinephrine, amphetamine, ephedrine and norepinephrine; and local anesthetics selected from the group including procaine, lidocaine, naepaine, piperocaine, tetracaine, and dibucane. Generically, the polymer agent formulations can contain from about 0.01% to about 40% by weight of agent including drug.

In another embodiment, the orthoester polymers are useful for coating agents that lend themselves to use as slow release fertilizers. The fertilizers are coated in their conventional form such as granules, powder, beads, particles, and the like. Fertilizers that can be coated include urea, fertilizers with slow ammonia release, fertilizers in the form of water soluble salts such as elements of carbon, nitrogen, phosphorous, sulfur, potassium, calcium, magnesium, manganese, zinc, copper, boron, and the like. Also, fertilizers such as the common fertilizers designated by 8-24-12, 8-8-6, 5-20-20, 12-12-12, 14-16-0, 8-4-6, 3-9-6, and the like. Additionally, the fertilizers or plant nutrient can be impregnated into, or suitably admixed with inert materials such as silica, coke, and the like.

In one embodiment, the polymers prepared according to the spirit of the invention are applied to the fertilizers, for example, in granular form, by mixing the fertilizer and the orthoester polymer in a fluidized bed having a conical bottom. The bed is equipped with an air inlet at the top for introducing air for mixing the polymer and fertilizer until the fertilizer is coated with 0.1% to 10% by weight of polymer. The temperature of the air is dependent on the concentration of the dispersion, usually 20° to 100° C. In another embodiment, the fertilizer is coated by mixing the polymer with an organic solvent to facilitate its application in thin coat form to the fertilizer granules. The selection of suitable solvents, in view of those set forth above, is within the skill of the art. The coating compositions can additionally contain pigments, dyes, driers, stabilizers, and the like.

In another embodiment, the polymers of the invention are useful for making articles of manufacture including devices releasing beneficial agents. The polymers can be processed into articles, including delivery devices, by standard manufacturing technqiues. For example, the polymers can be extruded into filaments, spun into fibers, pressed into shaped articles, solvent film cast, doctor-bladed into thin films, coated onto an agent by solvent evaporation, coated by using a fluidized bed, compression and transfer molded, and processed by like standard methods of manufacture. The polymers of the invention can be used as a single film, in a number of layers made of the same or of different polymers, and they can be made into devices of various geometric shapes, for example flat, square, round, tubular, disc, ring, and the like. Also, the devices of the invention are sized, shaped and adapted for implantation, insertion or placement on the body, in body cavities and passageways, or for positioning in other environments of use, for example, streams, aquariums, fields or reservoirs. Standard procedures for processing polymers are described in *Plastic Encyclopedia,* Vol. 46, pages 62 to 70, 1969. The polymers of the invention are useful for making devices for dispensing a beneficial agent, as they have a controlled degree of hydrophobicity in the environment of use and because they erode into innocuous products at a continuous rate which exhibits no known deleterious effects on the environment or towards an animal body.

While the invention pertains to polymers, and while these polymers and the method for making them have been described in detail for the nowpreferred embodiments, those skilled in the art will appreciate that various modifications, changes, additions and omissions in the invention can be made without departing from the spirit of the invention.

We claim:

1. A composition of matter comprising an orthoester polymer of the general formula:

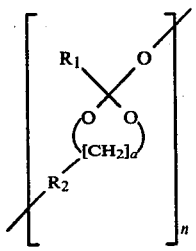

wherein $R_1$ is a member selected from the group consisting of hydrogen, alkyl of 1 to 20 carbon atoms, alkenyl of 2 to 20 carbon atoms, cycloalkyl of 3 to 8 carbon atoms, cycloalkyl of 3 to 8 carbon atoms substituted with a member selected from the group consisting of alkyl of 1 to 20 carbon atoms, alkenyl of 2 to 20 carbon atoms and alkoxy of 1 to 20 carbon atoms, cycloalkenyl of 4 to 8 carbon atoms, cycloalkenyl of 4 to 8 carbon atoms substituted with a member selected from the group consisting of alkyl of 1 to 20 carbon atoms, alkenyl of 2 to 20 carbon atoms and alkoxy of 1 to 20 carbon atoms, and aryl of 6 to 36 carbon atoms, $R_2$ is an arylene of 6 to 36 carbon atoms; a is 2 to 3, n is greater than 10, and from about 0.01% to about 40% by weight of a beneficial drug dispersed in said polymer, and wherein the drug is released at a controlled and continuous rate to a biological environment of use as the polymer erodes over a prolonged period of time.

2. The composition of matter comprising the orthoester polymer and the beneficial drug according to claim 1, wherein the drug is selected from the group consisting of analgesics, antipyretics, anti-inflammatory, hormonal, sympathomimetic, diuretic and ophthalmic drugs.

3. The composition of matter comprising the orthoester polymer and the beneficial drug according to claim 1, wherein the drug is selected from the group consisting of progestational and estrogenic steroids.

4. The composition of matter comprising the orthoester polymer and the beneficial drug according to claim 1, wherein the drug is an ophthalmic drug selected from the group consisting of pilocarpine and its therapeutically acceptable salts, eserine, salicylate, atropine, homatropine and eucatropine.

5. The composition of matter comprising the orthoester polymer and the beneficial drug according to claim 1, wherein the beneficial drug is a sympathomimetic drug selected from the group consisting of epinephrine, amphetamine, ephedrine and norepinephrine.

6. The composition of matter comprising the orthoester polymer and the beneficial drug according to claim 1, wherein the beneficial drug is a local anesthetic selected from the group consisting of procaine, lidocaine, naepaine, piperocaine, tetracaine, and dibucaine.

7. The composition of matter according to claim 1, wherein $R_2$ is a member selected from the group consisting of phenylene, and phenylene substituted with a member selected from the group consisting of alkyl of 1 to 20 carbon atoms, alkenyl of 2 to 20 carbon atoms, alkoxy of 1 to 20 carbon atoms and alkylene of 1 to 20 carbon atoms.

8. The composition of matter according to claim 1, wherein $R_2$ arylene is dialkylenearylene of 6 to 26 carbon atoms.

* * * * *